United States Patent [19]

Ohfune et al.

[11] Patent Number: 5,334,757
[45] Date of Patent: Aug. 2, 1994

[54] 2-(2,3-DICARBOXYCYCLOPROPYL) GLYCINE AND METHOD FOR PRODUCING THE SAME

[75] Inventors: Yasufumi Ohfune; Keiko Shimamoto, both of Osaka; Haruhiko Shinozaki; Michiko Ishida, both of Saitama, all of Japan

[73] Assignee: Suntory Limited, Osaka, Japan

[21] Appl. No.: 53,693

[22] Filed: Apr. 29, 1993

[30] Foreign Application Priority Data

Oct. 18, 1991 [JP] Japan .................................. 3-271392
Mar. 27, 1992 [JP] Japan .................................. 4-070472
Sep. 22, 1992 [JP] Japan .................................. 4-252823

[51] Int. Cl.[5] .......................................... C07C 229/46
[52] U.S. Cl. .................................................. 562/568
[58] Field of Search ........................................ 562/568

[56] References Cited

U.S. PATENT DOCUMENTS 3,293,176 12/1966 White ............................ 562/568 X
3,929,874 12/1975 Beermann et al. ............. 562/568 X
4,105,789 8/1978 Ondetti et al. ................. 562/568 X
4,959,493 9/1990 Ohfune et al. ...................... 562/506
5,095,114 3/1992 Radunz et al. ................. 562/568 X

OTHER PUBLICATIONS

K. Shimamoto et al., "Synthesis of 3′substituted 2 (carboxycyclopropy)glycines via intramolecular cyclopropanation. The folded form of L-Glutamate activates the non-MNDA receptor", Tetrahedron Letters, vol. 31, No. 28, 1990, Oxford GB, pp. 4049–52.

K. Shimamoto et al., "Synthesis of Four Diastereomeric L-2-(Carboxycyclopropl)glycines, Conformationally Constrained L-Glutamate Analogues", Reprinted from The Journal of Organic Chemistry, 1991, vol. 56.

M. Kawai et al., "2-Carboxycyclopropl)glycines: binding, neurotoxicity and induction of intracellular free $Ca^{2+}$ increase", European Journal of Pharmacology, 211 (1992) 195–202.

M. Ishida et al., "A potent metabotropic glutamate receptor agonist: electrophysiological actions of a conformationally restricted glutamate analogue in the rat spinal cord and Xenopus oocytes", Brain Research 637, (1990) 331–314.

*Primary Examiner*—Arthur C. Prescott
*Attorney, Agent, or Firm*—Cushman, Darby & Cushman

[57] ABSTRACT

(2S,1′R,2′R,3′R)-2-(2,3-dicarboxycyclopropyl)-glycine (DCG-I) and (2S,1′S,2′S,3′S)-2-(2,3-dicarboxycyclopropyl)glycine (DCG-II), as well as methods for synthesizing these compounds are provided. Studies on L-glutamate receptors with the use of DCG-I and DCG-II, which are agonists for NMDA receptors, contribute to the development of remedies for various nervous disorders. Further, DCG-I and DCG-II selectively inhibit monosynaptic reflex even at a low concentration, which makes them useful as a remedy for spastic palsy, an anesthetic and an analgesic.

5 Claims, No Drawings

2-(2,3-DICARBOXYCYCLOPROPYL) GLYCINE AND METHOD FOR PRODUCING THE SAME

DESCRIPTION

1. Technical Field

This invention relates to 2-(2,3-dicarboxycyclopropyl)-glycine and a method for producing the same. More particularly, it relates to cyclopropylglycine derivatives which play an important role in studies on L-glutamate receptors.

It is expected that the development of the compounds of the present invention would provide a clue for the development of antagonists for L-glutamate receptors and, in its turn, contribute to the therapeutics for neuropathy and nervous disorders such as epilepsy, Huntington's chorea, Alzheimer's disease and Parkinson's disease. It is further expected that the provision of the compounds of the present invention would give information which is important in revealing the reception mechanism in molecular level through the correlation between the conformations of L-glutamic acid and its analog and activities thereof.

2. Background Art

L-glutamic acid widely attracts attention as an excitatory neurotransmitter in the central nervous system of mammals, as a neuroexcitation toxin destroying nerve cells and inducing various diseases in nervous and brain and as a substance playing an important role in the construction of memory and learning.

L-glutamate receptors, which relate to the above-mentioned various physiological functions, are classified into the following three subtypes by introducing exogenous agonists:

(a) NMDA (N-methyl-D-aspartic acid) type,
(b) KA (kainic acid) type, and
(c) AMPA (α-amino-3-hydroxy-5-methyl-4-isoxazole propionic acid) type.

Alternately, the KA (kainic acid) type and the AMPA (α-amino-3-hydroxy-5-methyl-4-isoxazole propionic acid) type are sometimes combined together and classified as "non-NMDA type".

It has been suggested that NMDA type receptors are neuroexcitotoxic center. It is assumed that the excessive activation of these L-glutamate receptors causes death of nerve cells and, as a result, various nervous diseases are thus induced.

Regarding NMDA type receptors, the present inventors previously disclosed that (2S,1'R,2'S)-2-(2-carboxycyclopropyl)glycine is a potent agonist of the NMDA type superior to NMDA and that the folded conformation of glutamic acid activates NMDA receptors (refer to Japanese Patent Laid-Open No. 093563/1991).

Regarding non-NMDA type receptors, the present inventors also disclosed that (2S,1'R,2'R,3'R)-2-(2-carboxy-3-methoxymethylcyclopropyl)glycine and (2S,1'R,2'R,3'R)-2-(2-carboxy-3-benzyloxymethylcyclopropyl)glycine are agonists of the non-NMDA type [refer to Tetrahedron Letters, 31 (28), 4049–4052 (1990); and Brain Res., 550, 152–156 (1991)].

However, in order to develop these L-glutamate receptor agonists to pharmaceutical drugs, further investigations in novel agonists and new assay systems thereof are required.

SUMMARY OF THE INVENTION

The present inventors have further conducted extensive studies on agonists of L-glutamate receptors. We synthesized (2S,1'R,2'R,3'R)-2-(2,3-dicarboxycyclopropyl)glycine (hereinafter referred to simply as DCG-I) represented by the following formula (1):

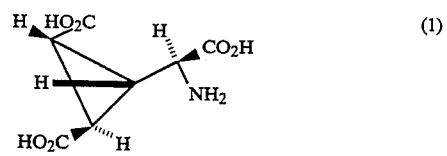

and (2S,1'S,2'S,3'S)-2-(2,3-dicarboxycyclopropyl)glycine (hereinafter referred to simply as DGC-II) represented by the following formula (2):

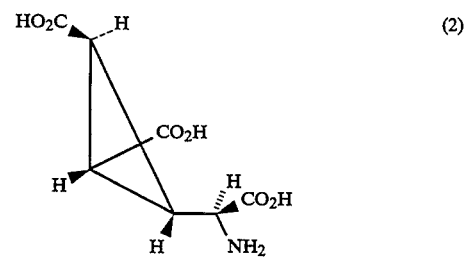

as a carboxycyclopropylglycine derivative which is fixed an extended conformation and a folded conformation in the same molecule and examined the agonistic activities of these compounds on L-glutamate receptors.

Further, the present inventors examined the inhibitory activities of these compounds on the monosynaptic reflex in the newborn rat spinal cord preparation.

As a result, the compounds of the present invention are NMDA-type agonists and have monosynaptic reflex inhibitory activity, thus completing the present invention.

DETAILED DESCRIPTION OF THE INVENTION

DCG-I, which is one of the compounds of the present invention, may be synthesized, for example, in accordance with the following scheme I.

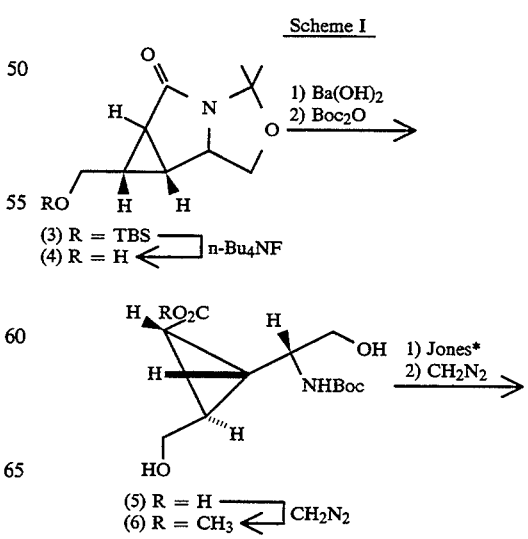

-continued
Scheme I

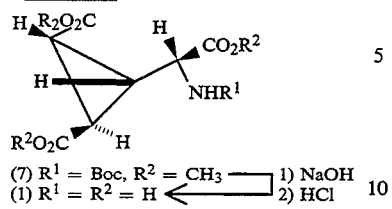

(7) R¹ = Boc, R² = CH₃ ⇌ 1) NaOH
(1) R¹ = R² = H       2) HCl

*Jones' reagent.

wherein

TBS represents a t-butyldimethylsilyl group; and
Boc represents a t-butoxycarbonyl group.

In the above scheme I, the t-TBS group in (1R,7S,8R,9R)-3-aza-9-t-butyl-dimethylsilyloxymethyl-4,4-dimethyl-5-oxatricyclo-[6.1.0.0³,⁷]nonan-2-one [described in Tetrahedron Letters, 31 (28), 4049-4052 (1990)] represented by the formula (3) is first removed by a known method to thereby give an alcohol represented by the formula (4).

The alcohol thus obtained is not purified but dissolved in water and ethanol. Then it is hydrolyzed with the use of an alkali such as 3 equivalents of barium hydroxide. After neutralizing with sulfuric acid and removing the insoluble materials by filtration, the filtrate is adjusted to pH 9 with triethylamine and then butoxycarbonylated by treating with di-t-butyl dicarbonate. Thus (2S,1'R,2'R,3'R)-N-t-butoxycarbonyl-2-(2-carboxy-3-hydroxymethylcyclopropyl)glycinol represented by the formula (5) is obtained.

Next, the product of the formula (5) is treated with diazomethane to thereby give a methyl ester, namely, (2S,1'R,2'R,3'R)-N-t-butoxycarbonyl-2-(2-methoxycarbonyl-3-hydroxymethylcyclopropyl)glycinol of the formula (6). The compound represented by the formula (6) is further successively treated with Jones' reagent and diazomethane to thereby give a trimethyl ester, namely (2S,1'R,2'R,3'R)-N-t-butoxycarbonyl-2-(2,3-dimethoxycarbonylcyclopropyl)glycine methyl ester represented by the formula (7). After hydrolyzing the compound of the formula (7), the target compound represented by the formula (1) is obtained.

Alternately, DCG-I may be highly stereo-selectively synthesized in a high yield in accordance with the following scheme Ia by using the compound 12a given in Scheme 2 in Tetrahedron Letters, 31 (28), 4051 (namely, the compound 13 in the following scheme Ia) as a starting compound.

Scheme Ia

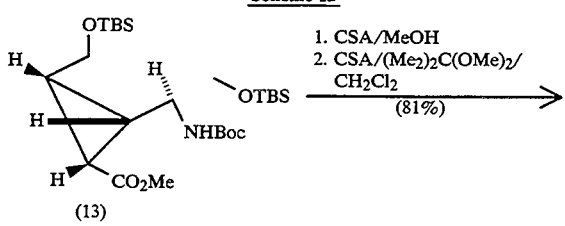

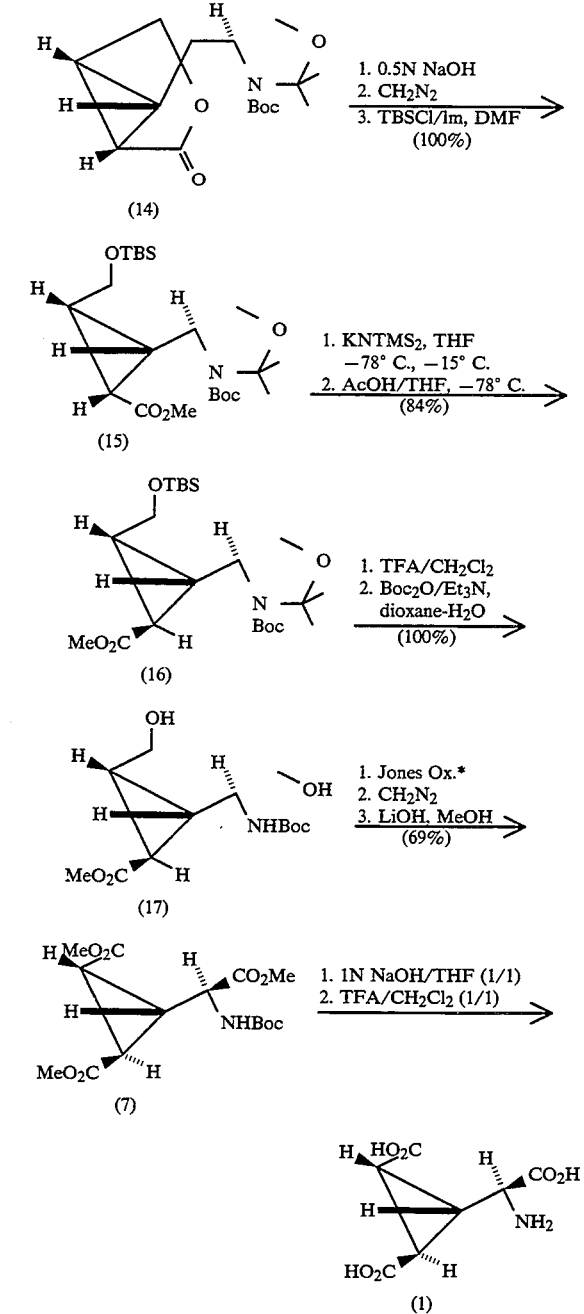

*Jones' reagent.

wherein TBS represents a t-butyldimethylsilyl group; Boc represents a t-butoxycarbonyl group; CSA represents (±)-10-camphorsulfonic acid; TBSCl represents t-butyldimethylsilyl chloride; Im represents imidazole; and KNTMS₂ represents potassium bistrimethylsilylamide.

According to the above scheme Ia, (2S,1'S,2'S, 3'R)-N-t-butoxycarbonyl-2-(3-t-butyldimethylsilyloxymethyl-2-methoxycarbonylcyclopropyl)glycinol t-butyldimethylsilyl ether represented by the formula (13) is treated with dl-camphorsulfonic acid and 2,2-dimethoxypropane. Thus (1S,5R,6S,4'S)-6-[N-(t-butoxycarbonyl)-2,2-dimethyl-1,3-oxazolidin-4-yl]-3-oxabicyclo[3.1.0]hexan-2-one represented by the formula (14) is obtained.

Next, the product of the formula (14) is hydrolyzed with an alkali and thus converted into a methyl ester. Then the hydroxyl group is protected again with a t-butyldimethylsilyl group to thereby give (4S,1'S,2'S,3'R)-N-t-butoxycarbonyl-2,2-dimethyl-4-[3-(t-butyldimethylsilyl)oxymethyl-2-methoxycarbonylcyclopropyl]-1,3-oxazolidine represented by the formula (15).

Subsequently, the product of the formula (15) is converted into (4S,1'S,2'R,3'R)-N-t-butoxycarbonyl-2,2-dimethyl-4-[3-(t-butyldimethylsily)oxymethyl-2-methoxycarbonylcyclopropyl]-1,3-oxazolidine represented by the formula (16) by treating with potassium bistrimethylsilylamide. After treating the obtained product with trifluoroacetic acid and di-t-butyl dicarbonate, (2S,1'S,2'R,3'R)-N-t-butoxycarbonyl-2-(2-methoxycarbonyl-3-hydroxymethylcyclopropyl)-glycinol represented by the formula (17) is obtained.

Next, the product of the formula (17) is subjected to Jones' oxidation, methyl-esterification and treatment with lithium hydroxide and thus (2S,1'R,2'R,3'R)-N-t-butoxycarbonyl-2-(2,3-dimethoxycarbonylcyclopropyl)glycine methyl ester represented by the formula (7) is obtained. Then this product is hydrolyzed and thus the compound represented by the formula (1) can be highly stereo-selectively synthesized in a high yield.

On the other hand, DCG-II, i.e., another compound of the present invention may be synthesized in accordance with the following scheme II, similar to the synthesis of DCG-I as described above.

Scheme II

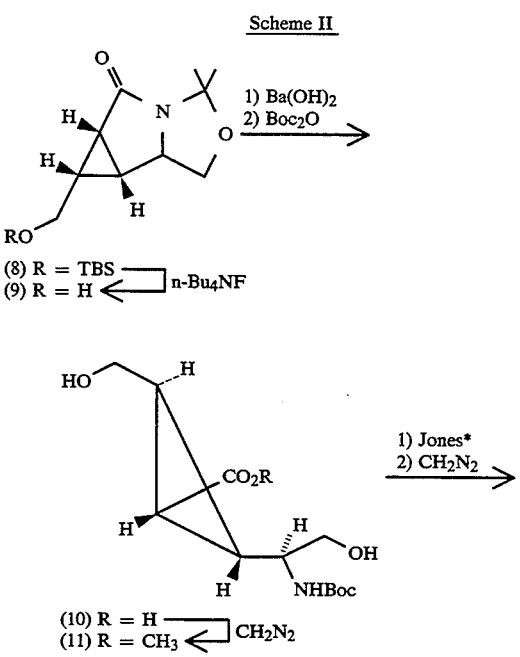

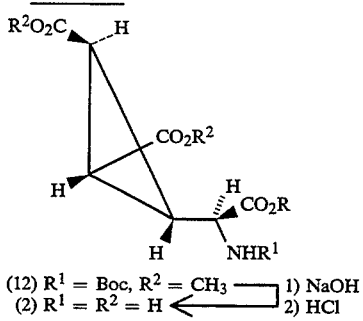

*Jones' reagent.

wherein
TBS represents a t-butyldimethylsilyl group; and
Boc represents a t-butoxycarbonyl group.

In the above scheme II, (1S,7S,8S,9S)-3-aza-9-t-butyldimethylsilyloxymethyl-4,4-dimethyl-5-oxatricyclo[6.1.0.0$^{3,7}$]-nonan-2-one [described in Tetrahedron Letters, 31 (28), 4049–4052 (1990)] represented by the formula (8) is used as a starting compound.

It is found out that DCG-I, which is one of the compounds of the present invention, is an agonist of the NMDA type in an electrophysiological assay with the use of a newborn rat spinal cord preparation.

It is also found out that DCG-II shows only a week agonistic activity of the NMDA type.

In a test of monosynaptic reflex inhibition in the newborn rat spinal cord preparation, furthermore, the compounds of the present invention inhibit the monosynaptic reflex at a ratio of 50% even at low concentration (DCG-I; $6.0 \times 10^{-8}$M, DCG-II; $1.0 \times 10^{-6}$M).

To further illustrate the present invention in more detail, the following Examples will be given. However, it is to be understood that the present invention is not restricted thereto.

EXAMPLE 1

Synthesis of (2S,1'R,2'R,3'R)-2-(2,3-dicarboxycyclopropyl)grycine (DCG-I) (1)

DCG-1 was synthesized in accordance with the above-mentioned scheme I.

Step 1: Synthesis of (2S,1'R,2'R,3'R)-N-t-butoxycarbonyl-2-(2-methoxycarbonyl-3-hydroxymethylcyclopropy)glycinol (6):

To a solution of 200 mg (0.64 mmol) of (1R, 7S, 8R, 9R)-3aza-9-t-butyl-dimethylsilyloxy-methyl-4,4-dimethyl-5-oxatricyclo[6.1.0.0$^{3,7}$]-nonan-2-one (3) in 2 ml of tetrahydrofuran (hereinafter referred to simply as THF) was added 1 ml of tetra-n-butylammonium fluoride (1M/THF solution) under ice-cooling and stirred for 10 minutes to give an alcohol (4).

The alcohol (4) thus obtained was not purified but dissolved in 2 ml of water and 2 ml of ethanol. Then 606 mg (1.92 mmol) of barium hydroxide was added and the mixture was stirred at 80° C. for 3 hours. After neutralizing with diluted sulfuric acid and removing the insoluble matters by filtration, the filtrate was adjusted to pH 9 with triethylamine.

Then 146 μl (0.64 mmol) of di-t-butyl dicarbonate and 2 ml of dioxane were added and the mixture was stirred at room temperature for 16 hours. After washing the reaction mixture with ether, the aqueous layer was adjusted to pH 1 with 1N hydrochloric acid and extracted with ethyl acetate. Then the organic layer was washed with a saturated aqueous solution of sodium chloride and dried over magnesium sulfate. After distilling off the solvent under reduced pressure, the compound of the formula (5) was obtained as an amorphous solid. Then a solution of diazomethane in ether was added to the solution of the compound (5) in ether to give a methyl ester. Thus the title compound (6) was quantitatively obtained.

The physical data of the compound (6) thus obtained were as follows.

Form: amorphous solid.
IR (cm$^{-1}$): 3392, 2988, 2884, 1726, 1716, 1708, 1696
$[\alpha]_D$: −38.6° (c0.75, CHCl$_3$)
$^1$H-NMR δ(ppm) (CDCl$_3$) (100 MHz): 1.44 (s, 9H), 1.48 (m, 1H), 1.74 (dd, 1H, J=6.9 Hz), 1.96 (m, 1H), 2.28 (s, 1H), 2.97 (m, 1H), 3.27 (m, 2H), 3.57 (m, 3H), 3.67 (s, 3H), 5.44 (brd, 1H, J=7 Hz)

Step 2: Synthesis of 2S,1'R,2'R,3'R)-N-t-butoxycarbonyl-2-(2,3-dimethoxycarbonylcyclopropyl)glycine methyl ester (7):

To a solution of 70 mg (0.24 mmol) of the methyl ester (6) obtained above in 2 ml of acetone was added Jones' reagent under ice-cooling. Then the mixture was stirred under ice-cooling for 1 hour and then at room temperature for additional 3 hours. Under ice-cooling, isopropyl alcohol was added to the solution to decompose the excess reagent, which was extracted with ethyl acetate. The organic layer was washed with a saturated aqueous solution of sodium chloride and dried over magnesium sulfate. After distilling off the solvent under reduced pressure, a solution of diazomethane in ether was added to the residue to give a methyl ester. Then the product was purified by silica gel column chromatography (methanol/chloroform=3/97) and thus 75 mg of the title compound (7) was obtained (yield: 90%).

The physical data of the compound (7) thus obtained were as follows.

Form: colorless crystals.
m.p.: 94.0°–95.0° C. (foaming decomp.)
IR (cm$^{-1}$): 3372, 2964, 1730
$[\alpha]_D$: +4.0° (c0.99, CHCl$_3$)
$^1$H-NMR δ(ppm) (CDCl$_3$) (100 MHz): 1.46 (s, 9H), 1.97 (ddd, 1H, J=6, 10, 10 Hz), 2.39 (dd, 1H, J=6, 10 Hz), 2.63 (t, 1H, J=6 Hz), 3.69 (s, 3H), 3.73 (s, 3H), 3.74 (s, 3H), 4.46 (dd, 1H, J=9, 10 Hz), 5.18 (brd, 1H, J=9 Hz)

Step 3: Synthesis of (2S,1′R, 2′R3′R)-2-(2,3-dicarboxycyclopropyl)glycine (DCG-I) (1):

To a solution of 58 mg (0.17 mmol) of the trimethyl ester (7) obtained above in 1 ml of THF was added 1 ml of a 1M aqueous solution of sodium hydroxide. The mixture was stirred under ice-cooling for 5 hours and then at room temperature for additional 24 hours. Next, to this solution was added 1 ml of 2N hydrochloric acid and stirred at room temperature for 18 hours. After concentration under reduced pressure, the residue was diluted with water and subjected to a column chromatography on Dowex 50 W×4, followed by washing with water and eluting with 1N aqueous ammonia. Then the aqueous ammonia was distilled off under reduced pressure and the residue was adjusted to pH 2 with 1N hydrochloric acid. After crystallizing from water/ethanol, 22 mg of the title compound was obtained (yield: 65%).

The physical data of the compound (1) thus obtained were as follows.

Form: colorless crystals.
m.p.: 174°–176° C. (foaming decomp.)
$[\alpha]_D$: −20.2° (c0.44, H$_2$O)
$^1$H-NMR δ(ppm) (D$_2$O) (270 MHz): 1.99 (ddd, 1H, J=5.9, 9.6, 10.2 Hz), 2.18 (dd, 1H, J=5.0, 5.9 Hz), 2.32 (dd, 1H, J=5.0, 9.6 Hz), 3.89 (d, 1H, J=10.2 Hz)
HR-MS (FAB): 204.0523 (calculated: 204,0508).

EXAMPLE 2

Synthesis of (2S,1'S,2'S,3'S)-2-2,3-dicarboxycyclopropyl)grycine (DCG-II) (2)

DCG-II was synthesized in accordance with the above scheme II, similar to the synthesis performed as shown in Example 1.

Starting from 300 mg (0.96 mmol) of (1S,7S,8S,9S)-3-aza-9-t-butyldimethylsilyloxymethyl-4,4-dimethyl-5-oxatricyclo-[6.1.0.0$^{3,7}$]-nonan-2-one (8), 82 mg of the trimethyl ester (12) was obtained in the same manner as the one employed in Example 1 (yield: 25%). From 65 mg (0.19 mmol) of the trimethyl ester (12) thus obtained, 10 mg of the title compound was obtained in the same manner (yield: 26%).

The physical data of the compound (2) thus obtained were as follows.

Form: colorless crystals.
m.p.: 153°–157° C. (foaming decomp.)
$[\alpha]_D$: +74.9° (c0.57, H$_2$O)
$^1$H-NMR δ(ppm) (D$_2$O) (270 MHz): 1.98 (ddd, 1H, J=5.5, 9.0, 10.5 Hz), 2.21 (dd, 1H, J=5.0, 9.0 Hz), 2.34 (dd, 1H, J=5.0, 5.5 Hz), 3.93 (d, 1H, J=10.5 Hz)
HR-MS (FAB): 204.0480 (calculated: 204.0508)

The physical data of the (2S,1'S,2'S,3'S)-N-t-butoxycarbonyl-2-(2-methoxycarbonyl-3-hydroxymethylcyclopropyl)glycinol (11), i.e., an intermediate in the synthesis, were as follows.

Form: amorphous solid.
IR (cm$^{-1}$): 3372, 2984, 2888, 1726, 1718, 1700, 1692
$[\alpha]_D$: −16.5° (c1.31, CHCl$_3$)
$^1$H-NMR δ(ppm) (CDCl$_3$) (100 MHz): 1.44 (s, 9H), 1.80 (m, 3H), 3.00 (br, 1H), 3.26 (d, 1H, J=8 Hz), 3.69 (s, 3H), 3.74 (m, 3H), 4.94 (d, 1H, J=8 Hz)

The physical data of (2S,1'S,2'S,3'S)-N-t-butoxycarbonyl-2-(2,3-dimethoxycarbonylcyclopropyl)glycine methyl ester, i.e., the intermediate (12) were as follows.

Form: oily substance.
IR (cm$^{-1}$): 3384, 2964, 1732
$[\alpha]_D$: +46.0° (c0.75, CHCl$_3$)
$^1$H-NMR δ(ppm) (CDCl$_3$) (100 MHz): 1.43 (s, 9H), 2.10 (ddd, 1H, J=6, 9, 9 Hz), 2.33 (dd, 1H, J=5, 9 Hz), 2.53 (t, 1H, J=5 Hz), 3.69 (s, 3H), 3.72 (s, 3H), 3.76 (s, 3H), 4.42 (t, 1H, J=9 Hz), 5.20 (brs, 1H)

EXAMPLE 3

Synthesis of (2S,1'R,2'R,3'R)-2-(2,3-dicarboxycyclopropyl)glycine (DCG-I) (1) (part 2):

Step 1: (1S,5R,6S,4'S)-6-[N-(t-butoxycarbonyl)-2,2-dimethyl-1,3-oxazolidin-4-yl]-3-oxabicyclo[3.1.0]hexan-2-one (14):

To a solution of 1.20 g (2.32 mmol) of (2S,1'S,2S,3'R)-N-t-butoxycarbonyl-2-(3-t-butyldimethylsilyloxymethyl-2-methoxycarbonylcyclopropyl)glycinol-t-butyldimethylsilyl ether (13) in 20 ml of methanol was added 20 mg of dlcamphorsulfonic acid. The mixture was stirred under a nitrogen gas stream at room temperature for 5 hours. After distilling off the solvent under reduced pressure, the residue was dissolved in 30 ml of methylene chloride and heated under reflux for 1 hour. Next, 15 ml of 2,2-dimethoxypropane was added to the reaction mixture, followed by heating under reflux again for 1.5 hours. After distilling off the solvent under reduced pressure, the residue was purified by silica gel column chromatography (methanol/chloroform=5/95) to thereby give a lactone (14). Yield: 560 mg (81%).

The physical data of this product (14) were as follows.

Form: colorless needless.
m.p.: 135.5°–136.0° C.
$[\alpha]_D$: −14.4° (c0.5, CHCl$_3$)
$^1$H-NMR (400 MHz, CDCl$_3$) δ(ppm): 1.50 (s, 9H), 1.52 (s, 3H), 1.74 (m, 1H), 2.24–2.34 (m, 2H), 3.77 (m, 1H), 3.89 (dd, 1H, J=1.4, 8.8 Hz), 4.06 (d, 1H, J=10.4 Hz), 4.07 (dd, 1H, J=6.0, 8.8 Hz), 4.38 (dd, 1H, J=5.3, 10.4 Hz)

Step 2: (4S,1′S,2′S,3′R)-N-t-butoxycarbonyl-2,2-dimethyl-4-[3-(t-butyldimethylsilyl)oxymethyl-2-methoxycarbonylcyclopropyl]-1,3-oxazolidine (15):

To a solution of 560 mg (1.89 mmol) of the lactone (14) in tetrahydrofuran (10 ml) was added 4.9 ml (2.45 mmol) of sodium hydroxide and the mixture was stirred at 0° C. for 16 hours. Then the reaction mixture was adjusted to pH 2 with 1N hydrochloric acid and extracted with ethyl acetate. The organic layer was washed with a saturated aqueous solution of sodium chloride and dried over magnesium sulfate. Removal of the solvent under reduced pressure gave an amorphous compound which was then esterified with a solution of diazomethane in ether. The resulting mixture was subjected to silica gel column chromatography (ether) to give a methyl ester. To the solution of this methyl ester in 7 ml of N,N-dimethylformamide was added a solution of 257 mg (3.78 mmol) of imidazole and 428 mg (2.84 mmol) of t-butyldimethylsilyl chloride in 5 ml of N,N-dimethylformamide. Then the mixture was stirred under a nitrogen gas stream at 0° C. for 30 minutes and then at room temperature for 2 hours. The reaction mixture was poured into ice/water and extracted with ether. The organic layer was washed with an aqueous solution of sodium chloride and dried over magnesium sulfate. After distilling off the solvent, the residue was purified by silica gel column chromatography (ether/hexane=7/93). Thus 2′S-methyl ester (15) was obtained. Yield: 865 mg (100%).

The physical data of this product (15) were as follows.

Form: oily substance.
$[\alpha]_D$: −56.0° (c0.5, CHCl$_3$)
$^1$H-NMR (400 MHz, CDCl$_3$) δ(ppm): 0.2 (s, 6H), 0.88 (s, 9H), 1.46 (s, 9H), 1.40–1.62 (m, 2H), 1.58 (s, 3H), 1.60 (s, 3H), 1.92 (dd, 1H, J=8.8, 8.8 Hz), 3.72 (s, 3H), 3.93 (brs, 1H), 4.03 (dd, 1H, J=5.8, 8.8 Hz), 4.10 (brs, 2H), 4.34 (brs, 1H)

Step 3: (4S,1′S,2′R,3′R)-N-t-butoxycarbonyl-2,2-dimethyl-4-[3-(t-butyldimethylsilyl)oxymethyl-2-methoxycarbonylcyclopropyl]-1,3-oxazolidine (16):

To a solution of 840 mg (1.9 mmol) of the 2′S-methyl ester (15) obtained above in 20 ml of tetrahydrofuran under a nitrogen gas stream at −78° C. was added dropwise 4.16 ml (2.08 mmol) of a 0.5M solution of potassium bistrimethylsilylamide. The reaction mixture was stirred at −78° C. for 30 minutes, at −15° C. for 1.5 hours and at −78° C. for 10 minutes. Then to the solution was added a solution of 148 mg (2.48 mmol) of acetic acid in tetrahydrofuran (2 ml). Water was added to the reaction mixture and then extracted with ether. The organic layer was washed with an aqueous solution of sodium chloride and dried over magnesium sulfate. After distilling off the solvent, the obtained residue was purified by silica gel column chromatography (ether/hexane=1/9) to give 2′R-methyl ester (16). Yield: 719 mg (84%).

The physical data of the product (16) thus obtained were as follows.

Form: colorless crystals.
m.p.: 92.0°–92.5° C.
$[\alpha]_D$: +7.5° (c0.8, CHCl$_3$)
$^1$H-NMR (400 MHz, CDCl$_3$) δ(ppm): 0.04 (s, 3H), 0.06 (s, 3H), 0.88 (s, 9H), 1.48 (s, 12H), 1.54 (s, 3H), 1.71 (m, 1H), 1.80 (m, 1H), 1.95 (m, 0.7H), 2.17 (m, 0.3H), 3.46 (dd, 1H, J=8.0, 10.5 Hz), 3.66 (s, 3H), 3.70 (m, 0.7H), 3.84 (m, 0.3H), 3.96 (dd, 1H, J=5.2, 8.5 Hz), 3.98 (m, 1H), 4.02 (dd, 1H, J=8.5, 8.5 Hz)

Step 4: (2S,1′S,2′R,3′R)-N-t-butoxycarbonyl-2-(3-hydroxymethyl-2-methoxycarbonylcyclopropyl)-glycinol (17):

To a solution of 480 mg (1.08 mmol) of the 2′R-methyl ester (16) in 4 ml of methylene chloride was added 4 ml of trifluoroacetic acid and the mixture was stirred at 0° C. for 1 hour and then at room temperature for 30 minutes. After concentrating the reaction mixture under reduced pressure, the residue was dissolved in 4 ml of dioxane and 4 ml of water, followed by adjusting the pH value to 9 by adding triethylamine. Then 1 ml of di-t-butyl dicarbonate was added to the solution obtained above and stirred at room temperature for 4 hours. After distilling off the solvent under reduced pressure, the residue was extracted with chloroform and ethyl acetate and dried over magnesium sulfate. After distilling off the solvent, the oily substance thus obtained was purified by silica gel column chromatography (ethyl acetate) to give the glycinol product (17). Yield: 315 mg (100%).

The physical data of this product were as follows.

Form: oily substance.
$[\alpha]_D$: +19.7° (c0.6, CHCl$_3$)
$^1$H-NMR (300 MHz, CDCl$_3$) δ(ppm): 1.44 (s, 9H), 1.60 (ddd, 1H, J=5.0, 9.0, 10.0 Hz), 1.98 (ddt, 1H, J=5.0, 5.0, 10.0, 10.0 Hz), 3.40–3.62 (m, 5H), 3.68 (s, 3H), 3.86 (1H, dd, J=4.1, 10.0 Hz), 4.02 (dd, 1H, J=5.0, 12.0 Hz)

Step 5: (2S,1′R,2′R,3′R)-N-t-butoxycarbonyl-2-(2,3-dimethoxycarbonylcyclopropyl)-glycine methyl ester (7):

To a solution of 315 mg (1.08 mmol) of the glycinol (17) obtained above in 20 ml of acetone was added Jones' reagent under ice-cooling. Then the mixture was stirred under ice-cooling for 2 hours and at room temperature for additional 2 hours. Then isopropyl alcohol was added to decompose the excess reagent and a saturated solution of sodium chloride was added, followed by extracting with chloroform and ethyl acetate. The organic layer was washed with an aqueous solution of sodium chloride and dried over magnesium sulfate. After distilling off the solvent, the residue thus obtained was esterified by adding a solution of diazomethane in ether. After distilling off the ether, the residue was dissolved in 10 ml of methanol. To this solution was then added 10 mg of lithium hydroxide and the mixture was stirred at room temperature for 30 minutes. Then the reaction mixture was neutralized by adding several drops of acetic acid and the solvent was distilled off under reduced pressure. After purification by silica gel column chromatography (ether/hexane=1/1), trimethyl ester (7) was obtained. Yield: 309 mg (69%).

The physical data of this product (7) were as follows.
Form: colorless crystals.
m.p. 94.0°-95.9° C. (foaming decomp.).
IR (cm$^{-1}$): 3372, 2964, 1730
$[\alpha]_D$+4.0° (c0.99, CHCl$_3$)
$^1$H-NMR (270 MHz, CDCl$_3$) δ(ppm): 1.46 (s, 9H), 1.91 (ddd, 1H, J=6.0, 9.5, 10.5 Hz), 2.33 (dd, 1H, J=5.0, 9.5 Hz), 2.58 (dd, 1H, J=5.0, 6.0 Hz), 3.69 (s, 3H), 3.73 (s, 3H), 3.75 (s, 3H), 4.42 (dd, 1H, J=9, 10.5 Hz), 5.18 (brs, 1H)

Step 6: (2S,1'R, 2'R, 3'R)-2-(2,3-dicarboxycyclopropyl)glycine (DCG-I) (1):

To a solution of 58 mg (0.17 mmol) of the trimethyl ester (7) obtained above in 1 ml of THF was added 1 ml of a 1M aqueous solution of sodium hydroxide. The mixture was stirred under ice-cooling for 5 hours and then at room temperature for additional 24 hours. After adding 1 ml of 2N hydrochloric acid, the mixture was further stirred at room temperature for 18 hours. After concentrating under reduced pressure, the residue thus obtained was diluted with water and subjected to column chromatography on Dowex 50 W ×4. Then it was washed with water and eluted with 1N aqueous ammonia. After distilling off the aqueous ammonia under reduced pressure, the residue was adjusted to pH 2 with 1N hydrochloric acid. Recrystallization from water/methanol gave the target t-DCG-I (1). Yield: 22 mg (65%).

The physical data of the target product (1) were as follows.
Form: colorless crystals.
m.p.: 174°-176° C. (foaming decomp.).
$[\alpha]_D$: −20.2° (c 0.44, H$_2$O)
$^1$H-NMR (270 MHz, D$_2$O) δ(ppm): 1.99 (ddd, 1H, J=5.9, 9.6, 10.2 Hz), 2.18 (dd, 1H, J=5.0, 5.9 Hz), 2.32 (dd, 1H, J=5.0, 9.6 Hz), 3.89 (d, 1H, J=10.2 Hz)
HR-MS (FAB): 204.0523 (calculated: 204.0508).

TEST EXAMPLE 1

Measurement of depolarizing activity:

The depolarizations induced by DCG-I and DCG-II on a newborn rat spinal cord preparation were measured in accordance with the method of Shinozaki et al., [refer to Br. J. Pharmacol., 98, 1213-1224 (1989)]. Namely, a newborn rat spinal cord preparation was used and extracellular records of the depolarizing activities from the anterior roots of motor nerve cells, under perfusion of an artificial physiological solution (spinal fluid) containing 0.5 μM of tetrodotoxin, of L-glutamic acid and the compounds of the present invention were measured over a concentration range of from $10^{-3}$ to $10^{-7}$M. Thus the minimum effective concentration (MEC) of each compound was determined.

Table 1 summarizes the results.

TABLE 1

| Compound | MEC (M) | Activity ratio |
|---|---|---|
| L-glutamic acid | $1 \times 10^{-4}$ | 1 |
| DCG-I | $3 \times 10^{-6}$ | 33 |
| DCG-II | $2 \times 10^{-4}$ | 0.5 |

Next, the above procedure was repeated except that an artificial physiological solution (spinal fluid) containing $3 \times 10^{-5}$M of 3-[(±)-2-carboxypiperazin-4-yl]-propyl-1-phosphonic acid (hereinafter referred to simply as CPP) was perfused. As a result, it was observed that the depolarization of both of DCG-I and DCG-II were completely inhibited by adding $3 \times 10^{-5}$M of CPP. Thus both of DCG-I and DCG-II were regarded as agonists for NMDA receptors.

TEST EXAMPLE 2

Determination of monosynaptic reflex inhibition activity

Monosynaptic reflex in the newborn rat spinal cord preparation was measured by the method reported by Otsuka et al., [refer to M. Otsuka, Seitai no Kagaku, 36 (4), 325-327].

The spinal cord of a newborn Wister rat was taken out, as encircled by the spinal column, under etherization. Then it was immersed in an artificial spinal solution saturated with 95% of oxygen and 5% of carbon dioxide gas and a semi-incised spinal cord preparation having from L3 to L5 anterior roots and posterior roots adhering thereto as such was prepared under a stereomicroscope. The semi-incised spinal cord preparation thus obtained was transferred into a perfusion chamber and perfused with an artificial spinal solution saturated with 95% of oxygen and 5% of carbon dioxide gas.

A single stimulation was applied to a posterior root via a suction electrode and the anterior root reflection potential of the corresponding anterior root was recorded. Thus a spike was observed at an early stage followed by slow depolarization accompanied by asynchronous changes in potential. The above-mentioned spike at the early stage corresponded to the monosynaptic reflex [refer to Konishi, S, Advances in Pharmacology and Therapeutics II, Pergamon, Oxford, Vol. 2, 255-260 (1982)].

DCG-I and DCG-II at various concentration were added to the perfusion solution and the monosynaptic reflexes thus caused were measured. Thus the 50% inhibitory concentration (IC$_{50}$) of each test compound was determined.

Table II shows the results.

TABLE II

| Monosynaptic reflex inhibition activity | |
|---|---|
| Compound | IC$_{50}$ (M) |
| DCG-I | $6.0 \times 10^{-8}$ |
| DCG-II | $1.0 \times 10^{-6}$ |

In contrast, it is reported that the IC$_{50}$ of Baclofen, which is a gamma-aminobutyric acid derivative employed as a remedy for spastic palsy caused by trauma in the brain, is about $5 \times 10^{-7}$M (500 nM). Accordingly, the results given above indicate that DCG-I and DCG-II would inhibit (50%) monosynaptic reflex respectively at concentrations about 1/20 and twice as much as the IC$_{50}$ of Baclofen. Thus it is strongly suggested that the compound of the present invention are useful as a remedy for spastic palsy, an anesthetic and an analgesic.

According to the present invention, (2S, 1'R, 2'R, 3'R)-2-(2,3-dicarboxycyclopropyl)glycine (DCG-I) (1) and (2S, 1'S, 2'S, 3'S)-2-(2,3-dicarboxycyclopropyl)glycine (DCG-II) (2), which are both agonists for NMDA receptors, can be synthesized.

The above-mentioned DCG-I and DCG-II, which are agonists for NMDA receptors, can provide valuable information relating investigations on L-glutamate receptors. Further, the development of agonists and antagonists for L-glutamate receptors would contribute to the development of remedies for various nervous disorders. Furthermore, DCG-I and DCG-II selectively inhibit monosynaptic reflex even at a low concentration, which makes them useful as a remedy for spastic palsy, an anesthetic and an analgesic.

We claim:

1. (2S, 1'R, 2'R, 3'R)-2-(2,3-dicarboxycyclopropyl)glycine represented by the following formula (1):

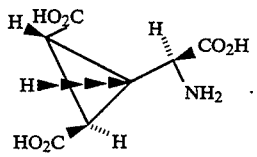

2. (2S, 1'S, 2'S, 3'S)-2-(2,3-dicarboxycyclopropyl)glycine represented by the following formula (2):

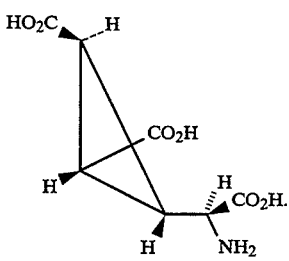

3. A method for producing (2S, 1'R, 2'R, 3'R)-2-(2,3-dicarboxycyclopropyl)glycine represented by the following formula (1):

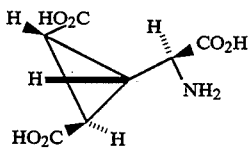

which comprises:
(a) removing the t-butyldimethylsilyl group of (1R, 7S, 8R, 9R)-3-aza-9-t-butyldimethylsilyloxymethyl-4,4-dimethyl-5-oxatricyclo-[6.1.0.0$^{3,7}$]nonan-2-one represented by the following formula (3):

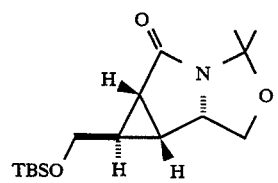

wherein TBS represents a t-butyldimethylsilyl group; to thereby give an alcohol represented by the following formula (4):

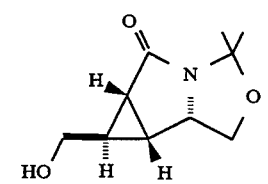

(b) next, hydrolyzing said alcohol with an alkali and then t-butoxycarbonylating to thereby give (2S, 1'R, 2'R, 3'R)-N-t-butoxycarbonyl-2-(2-carboxy-3-hydroxymethylcyclopropyl)glycinol represented by the following formula (5):

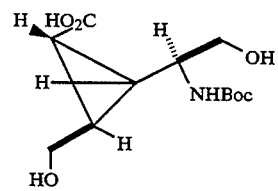

wherein Boc represents a t-butoxycarbonyl group;
(c) next, converting the compound of the formula (5) into a methyl ester to thereby give (2S, 1'R, 2'R, 3'R)-N-t-butoxycarbonyl-2-(2-methoxycarbonyl-3-hydroxymethylcyclopropyl)glycinol represented by the following formula (6):

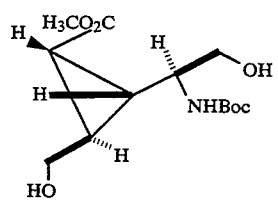

(d) next, oxidizing said alcohol to thereby give a carboxylic acid and then converting the obtained carboxylic acid into a methyl ester to thereby give (2S,1'R,2'R,3'R)-N-t-butoxycarbonyl-2(2,3-dimethoxycarbonylcyclopropyl)glycine methyl ester represented by the following formula (7):

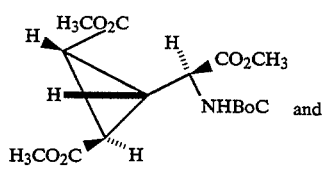

(e) finally, hydrolyzing said ester to thereby give the compound of the formula (1).

4. A method for producing (2S, 1'S,2'S,3'S)-2-(2,3-dicarboxycyclopropyl)glycine represented by the following formula (2):

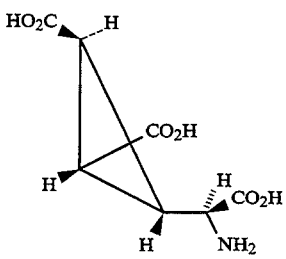

which comprises:
(a) removing the t-butyldimethylsilyl group of (1S,7S,8S,9S)-3-aza-9-t-butyldimethylsilyloxymethyl-4,4-dimethyl-5-oxatricyclo-[6.1.0.0$^{3,7}$]nonan-2-one represented by the following formula (8):

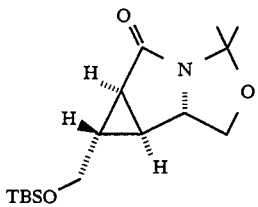

(8)

wherein TBS represents a t-butyldimethylsilyl group; to thereby give an alcohol represented by the following formula (9):

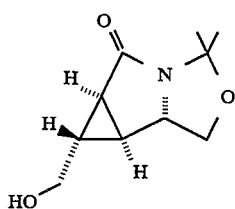

(9)

(b) next, hydrolyzing said alcohol with an alkali and then t-butoxycarbonylating to thereby give (2S,1'S,2'S, 3'S)-N-t-butoxycarbonyl-2-(2-carboxy-3-hydroxymethylcyclopropyl)glycinol represented by the following formula (10):

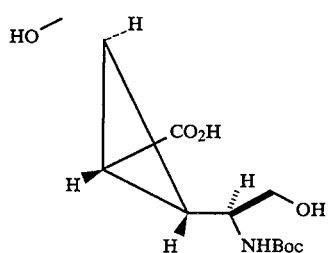

(10)

wherein Boc represents a t-butoxycarbonyl group;
(c) next, converting the compound of the formula (10) into a methyl ester to thereby give (2S,1'S,2'S,3'S)-N-t-butoxycarbonyl-2-(2-methoxycarbonyl-3-hydroxymethylcyclopropyl)glycinol represented by the following formula (11):

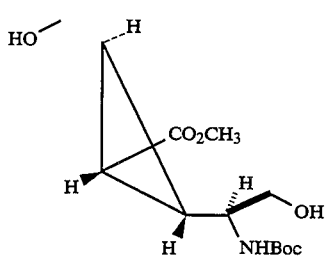

(11)

(d) next, oxidizing said alcohol to thereby give a carboxylic acid and then converting the obtained carboxylic acid into a methyl ester to thereby give (2S,1'S,2'S,3'S)-N-t-butoxycarbonyl-2(2,3-dimethoxycarbonylcyclopropyl)glycine methyl ester represented by the following formula (12):

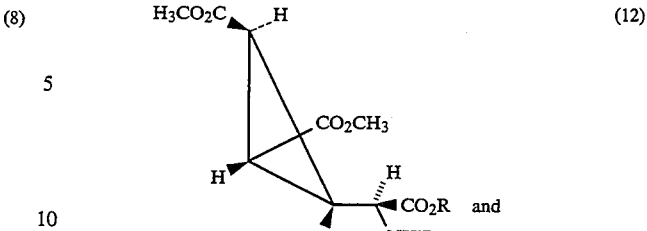

(12)

(e) finally, hydrolyzing said ester to thereby give the compound of the formula (2).

5. A method for producing (2S,1'R,2'R,3'R)-2-(2,3-dicarboxycyclopropyl)glycine represented by the following formula (1):

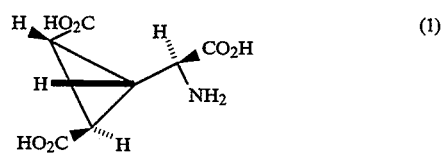

(1)

which comprises:
(a) treating (2S,1'S,2'S,3'R)-N-t-butoxycarbonyl-2-(3-t-butyldimethylsilyloxymethyl-2-methoxycarbonylcyclopropyl) glycinol-t-butyldimethylsilyl ether represented by the following formula (13):

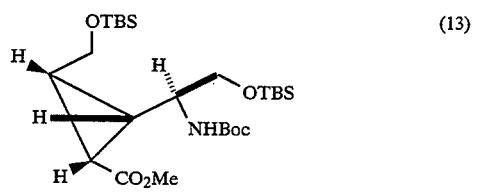

(13)

wherein
TBS represents a t-butyldimethylsilyl group; and
Boc represents a t-butoxycarbonyl group; with dl-camphorsulfonic acid and 2,2-dimethoxypropane to thereby give (1S,5R,6S,4'S)-6-[N-(t-butoxycarbonyl)-2,2-dimethyl-1,3-oxazolidin-4-yl]-3-oxabicyclo[3.1.0]hexan-2-one represented by the following formula (14):

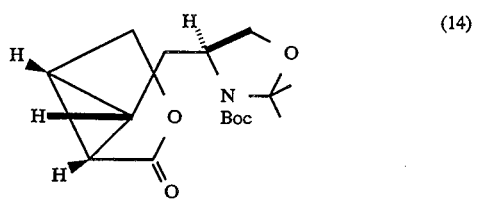

(14)

wherein Boc represents a t-butoxycarbonyl group;
(b) next, hydrolyzing the obtained compound of the formula (14) with an alkali, converting into a methyl ester and then protecting the hydroxyl group with a t-butyldimethylsilyl group again to thereby give (4S,1'S,2'S,3'R)-N-t-butoxycarbonyl-2,2-dimethyl-4-[3-(t-butyldimethylsilyl)oxymethyl-2-methoxycarbonyl-cyclopropyl]-1,3-oxazolidine represented by the following formula (15):

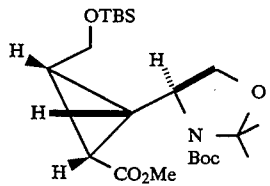
(15)

wherein
TBS represents a t-butyldimethylsilyl group; and
Boc represents a t-butoxycarbonyl group;

(c) next, treating the compound of the formula (15) with potassium bistrimethylsilylamide to thereby convert it into (4S,1'S,2'R,3'R)-N-t-butoxycarbonyl-2,2-dimethyl-4-[3-(t-butyldimethylsilyl)oxymethyl-2-methoxycarbonylcyclopropyl]-1,3-oxazolidine represented by the following formula (16):

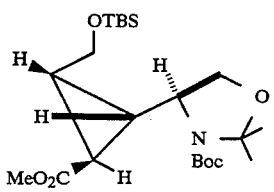
(16)

wherein
TBS represents a t-butyldimethylsilyl group; and
Boc represents a t-butoxycarbonyl group;

(d) next, treating the compound of the formula (16) with trifluoroacetic acid and di-t-butyl dicarbonate to thereby give (2S,1'S,2'R,3'R)-N-t-butoxycarbonyl-2-(3-hydroxymethyl-2-methoxycarbonylcyclopropyl)glycinol represented by the following formula (17):

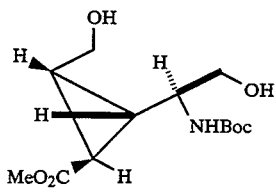
(17)

wherein
TBS represents a t-butyldimethylsilyl group; and
Boc represents a t-butoxycarbonyl group;

(e) then, converting the compound of the formula (17) into (2S,1'R,2'R,3'R)-N-t-butoxycarbonyl-2-(2,3-dimethoxycarbonyl-cyclopropyl)glycine methyl ester represented by the following formula (7):

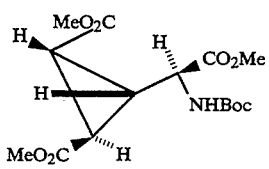
(7)

wherein Boc represents a t-butoxycarbonyl group; via Jones' oxidation, methyl-esterification and treatment with lithium hydroxide; and (f) finally, hydrolyzing the compound of the formula (7) to thereby give the above-mentioned compound represented by the formula (1).

* * * * *

UNITED STATES PATENT AND TRADEMARK OFFICE
CERTIFICATE OF CORRECTION

PATENT NO. : 5,334,757
DATED : August 2, 1994
INVENTOR(S) : Ohfune et al.

It is certified that error appears in the above-indentified patent and that said Letters Patent is hereby corrected as shown below:

On the title page, should read:

[63] PCT/JP92/01351 October 16, 1992

Signed and Sealed this

Twenty-third Day of September, 1997

Attest:

BRUCE LEHMAN

Attesting Officer    Commissioner of Patents and Trademarks